(12) United States Patent
Goodbread

(10) Patent No.: US 9,995,715 B2
(45) Date of Patent: Jun. 12, 2018

(54) ELECTROMAGNETIC TRANSDUCER FOR EXCITING AND SENSING VIBRATIONS OF RESONANT STRUCTURES

(71) Applicant: Rheonics GmbH, Winterthur (CH)

(72) Inventor: Joseph H. Goodbread, Winterthur (CH)

(73) Assignee: RHEONICS GMBH, Winterthur (CH)

( * ) Notice: Subject to any disclaimer, the term of this patent is extended or adjusted under 35 U.S.C. 154(b) by 358 days.

(21) Appl. No.: 14/685,365

(22) Filed: Apr. 13, 2015

(65) Prior Publication Data

US 2016/0011012 A1    Jan. 14, 2016

Related U.S. Application Data

(60) Provisional application No. 61/978,905, filed on Apr. 13, 2014.

(51) Int. Cl.
*G01N 11/16* (2006.01)
*G01N 29/036* (2006.01)
(Continued)

(52) U.S. Cl.
CPC ......... *G01N 29/036* (2013.01); *G01D 5/2006* (2013.01); *G01N 11/16* (2013.01);
(Continued)

(58) Field of Classification Search
CPC .. G01N 9/002; G01N 2009/006; G01N 11/16; G01N 11/162; E21B 49/08; E21B 2049/085
See application file for complete search history.

(56) References Cited

U.S. PATENT DOCUMENTS

| 3,935,726 A | 2/1976 | Heinz |
| 4,135,826 A | 1/1979 | Holm |

(Continued)

FOREIGN PATENT DOCUMENTS

| JP | 03146847 A | 6/1991 |
| JP | 07072063 A | 3/1995 |

OTHER PUBLICATIONS

Agoston, Evaluation of a vibrating micromachined cantilever sensor for measuring the viscosity of complex organic liquids, Sciencedirect.com, Elsevier, Sensors and Actuators, 2005, Vienna, Austria.

(Continued)

*Primary Examiner* — Blake A Tankersley
(74) *Attorney, Agent, or Firm* — Timothy E. Siegel Patent Law, PLLC; Timothy E. Siegel

(57) ABSTRACT

A fluid properties measurement device, including a magnetically excited and sensed resonator and a resonator electromagnetic excitation assembly, including an excitation coil driven by an electrical network, electrically connected to the excitation coil. The excitation coil is positioned so that a varying magnetic field produced by the excitation coil will drive the resonator in a pattern of resonating movement that has predetermined characteristics. Also, an electromagnetic sensing assembly, including a gradiometric sense coil is positioned so that an electromagnetic field originating due to movement of the resonator in a pattern having the predetermined characteristics, will create a time-varying gradient across the sense coil. Finally, a signal sensing electrical network is electrically connected to the sense coil.

20 Claims, 6 Drawing Sheets

(51) Int. Cl.
*G01N 29/24* (2006.01)
*G01D 5/20* (2006.01)

(52) U.S. Cl.
CPC ....... *G01N 11/162* (2013.01); *G01N 29/2412* (2013.01); *G01N 2291/014* (2013.01); *G01N 2291/02818* (2013.01); *G01N 2291/0426* (2013.01); *G01N 2291/101* (2013.01)

(56) References Cited

U.S. PATENT DOCUMENTS

| | | | |
|---|---|---|---|
| 4,655,075 A | | 4/1987 | Albert et al. |
| 5,596,139 A | | 1/1997 | Miura et al. |
| 5,837,885 A | | 11/1998 | Goodbread et al. |
| 6,018,988 A | * | 2/2000 | Persson .................. G01N 11/16 73/54.25 |
| 6,487,864 B1 | * | 12/2002 | Platt ........................ F25B 21/02 62/3.2 |
| 6,494,079 B1 | | 12/2002 | Matsiev et al. |
| 7,434,457 B2 | | 10/2008 | Goodwin et al. |
| 8,291,750 B1 | | 10/2012 | Goodbread et al. |
| 8,752,416 B2 | | 6/2014 | Goodbread et al. |
| 2011/0167910 A1 | * | 7/2011 | Storm ....................... G01F 1/74 73/32 A |
| 2014/0001984 A1 | * | 1/2014 | Kuisma ................ H02N 11/006 318/116 |

OTHER PUBLICATIONS

Goodwin, A Vibrating Edge Supported Plate, Fabricated by the Methods of Micro Electro Mechanical System for the Simultaneous Measurement of Density and Viscosity: Results for Methylbenzene and Octane at Temperatures between (323 and 423) K and Pressures in the Range (0.1 to 68) MPa, Journal of Chemical and Engineering Data, 2006, vol. 51, No. 1, U.S.

Requa, Electromechanically driven and sensed parametric resonance in silicon microcantilevers, Applied Physics Letters, 2006, vol. 88, Issue 26, CA, U.S.

* cited by examiner

ELECTROMAGNETIC TRANSDUCER FOR EXCITING AND SENSING VIBRATIONS OF RESONANT STRUCTURES

RELATED APPLICATIONS

This application claims priority from provisional application No. 61/978,905, filed Apr. 13, 2014, which is also incorporated by reference as if fully set forth herein.

BACKGROUND

Fluid properties sensors are known that make use of the interaction of a vibrating element with the fluid in which it is in contact. Among those sensors are those that make use of torsional resonators, and among those torsional resonator systems are those that are both driven and sensed by means of electromagnetic transducers.

Compared to piezoelectrically driven and sensed resonators, those with magnetic transducers are more robust and more stable over time, particularly with respect to temperature variations. In particular, sensors that are used in extreme environments, as for downhole fluid measurement in oil, gas, and geothermal drilling and well logging, may be exposed to pressures in excess of 2000 bar and temperatures of 200° C.

Patent application WO/2012/012508 describes coupled torsional resonators that incorporate magnets in their resonant structures that are driven and sensed by coils external to the resonator. The resonator is immersed in the fluid, while the coils may be placed outside the conduit containing the fluid, possibly in a chamber that is nominally at atmospheric pressure, so that the coils and their electrical connections are protected from the fluid. This obviates the need for electrical pressure feed-throughs and other sealing devices that are susceptible to degradation and failure.

Patent application WO/2012/012508 and related filings disclose means for exciting and sensing vibrations of the torsional resonator by means of either permanent magnets, or soft magnetic materials embedded in the oscillating parts of the sensor. The disadvantage of permanent magnets is that they may attract magnetic particles from the fluids in which they are immersed, which then adhere to the surface of the sensor and distort said sensor's readings.

Another method for measuring viscosity and possibly other properties of fluids is disclosed in US patent application 2013/0167620. That method includes a torsional resonator whose vibrations are excited by and sensed by a coil acting upon and acted upon by the field of a permanent magnet attached to the resonator, with the coils being a short distance away from the resonator.

In these and many other embodiments of electromagnetically sensed resonators, it is advantageous to make the sensing system as sensitive as possible in order to be able to measure the smallest expected amplitudes of vibration of the resonator. It is advantageous to measure very small amplitudes in the following circumstances:

1) Available driving force for the resonator is limited, either because of unavoidably large distance between the driving means and the resonator, or restricted available driving power (for instance, when operating in explosive atmospheres, to ensure intrinsically safe operation).

2) It is desired to operate a resonant fluid properties sensor over a very large range of amplitudes, so as to estimate non-Newtonian behavior of the fluid.

3) It is necessary to use soft magnetic materials rather than permanent magnets in the transducers driving and sensing the resonator. Such materials typically have much lower magnetic energy than do permanent magnets, requiring much more sensitive sensing means.

4) A fluid properties sensor with electromagnetic sensors must be operated in an environment where substantial magnetic fields are generated by nearby equipment such as electrical motors, transformers, and the like, such that said fields are capable of producing transducer outputs that would overwhelm the signals of interest.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a fluid properties measurement device, including a magnetically actuated and sensed resonator and a resonator electromagnetic excitation assembly, including an excitation coil and an excitation coil driving electrical network, electrically connected to the excitation coil. The excitation coil is positioned so that a varying magnetic field produced by the excitation coil will drive the resonator in a pattern of resonating movement that has predetermined characteristics. Also, an electromagnetic sensing assembly, including a gradiometric sense coil is positioned so that a magnetic field originating due to movement of the resonator in a pattern having the predetermined characteristics, will create a time-varying magnetic field gradient across the sense coil. Finally, a sense coil sensing electrical network is electrically connected to the sense coil.

In a second separate aspect the present invention is a method of sensing properties of a fluid that utilizes a measurement apparatus that includes a magnetically actuated and sensed resonator, an excitation coil and a gradiometric sense coil. First, the resonator is placed in the fluid. Then, the excitation coil is driven to create a varying magnetic field, thereby causing the resonator to resonate. Finally, the current produced by the gradiometric sense coil, in response to the resonator resonating, is measured and analyzed.

In addition to the exemplary aspects and embodiments described above, further aspects and embodiments will become apparent by reference to the drawings and by study of the following detailed descriptions.

Figure 1:
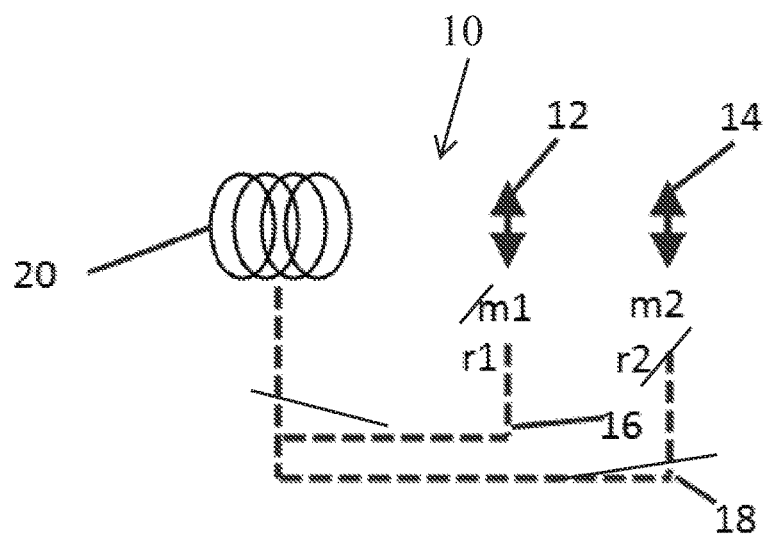
FIG. 1 is an illustration of distances to a coil of two different magnets, to help explain the concept of a gradiometric coil.

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

This application describes improvements to, among others, the sensor disclosed in the cited applications in which soft magnetic materials are used in the place of permanent magnets. In particular it discloses a coil structure advantageous for exciting and sensing the resonator. It is furthermore useful for exciting and sensing resonance of other resonant sensors under conditions that will be explained in the following disclosure.

The present application includes both a coil structure and an electronic amplifier system to permit using resonant transducers under unfavorable conditions including:

1. in the presence of strong AC magnetic fields that can induce signals in the sensing coils that can overwhelm the signals of interest;

2. in the case where the excitation and sense coils must be embedded in, or in close proximity to, conductive materials, since the excitation field can induce eddy currents in said conductive materials, which eddy currents then induce spurious signals in the sensing coils, disturbing or overwhelming the signals of interest; and 3. in the case where it is otherwise advantageous to wind both excitation and sensing coils on a common axis, in which case the fields from the excitation coil can induce large unwanted voltages in the sensing coil, leading to saturation of succeeding amplifier stages.

Two or more of these conditions may occur simultaneously. The unwanted effects produced by these conditions are disturbing in proportion to the electromagnetic sensitivity of the sense coils, so that they limit the useful amplitude range of the sensor.

This invention replaces the conventional sense coil—a simple winding with either an air core or a permeable core of ferrite, iron, or some other permeable material—with a so-called gradiometric coil. A gradiometric coil in its simplest form is composed of two windings, wound in opposite sense, on a common axis, and separated by an axial distance x. The two oppositely wound sections are connected in series, such that voltages induced in the two coils are subtracted from one another.

In the case that the two coils are immersed in a substantially uniform varying magnetic field, the voltages induced in the two coils cancel, and the coil produces no output. In the contrasting case, in which a source of a varying magnetic field is placed very close to one section of the composite coil, along the mutual axis of the two coils, the divergence of the field will result in a smaller voltage being induced in the coil section that is further away from the source than in the section that is closer to the source. The composite coil will therefore be preferentially sensitive to fields with a large field gradient than to those with small gradients.

In the case of the present application, the source of the varying field is generally a small magnetic object in the vicinity of the composite coil—generally at a distance comparable to the length of the composite coil—so that its field gradient is significant in the vicinity of the composite coil, and the coils will produce a significant voltage when the magnetic object is moved, as through the resonant vibration of the sensor of which it is a part.

When, however, the source of the magnetic field is far from the sensor assembly, as for example an electric motor operating some tens of centimeters from the sensor assembly, the field gradient of the remote source will be very small at the location of the gradiometric sensing coil, resulting in a vanishingly small voltage being induced in the composite coil. In the first instance, therefore, the gradiometric coil assembly is useful for reducing interference from neighboring sources of varying magnetic fields.

In a second instance, it may be that the excitation and sense coils are embedded in a metallic body, or are in close proximity to conductive materials. In that case, the field of the excitation coil induces eddy currents in the surrounding conductive material; these currents have a characteristic decay time causing them to persist after the excitation has been switched off. The eddy currents induce varying magnetic fields in the space around the coil assembly, which in turn induce spurious voltages in the sense coils during the time when the vibrational motion of the resonator is being measured. This can lead to errors in the received signals.

The gradiometric sense coil is of use in reducing interference from eddy currents in two ways. First, the excitation coil is located some distance from the sense coil, as when the excitation and sense coils are placed on opposite sides of the oscillating member. In that case, eddy currents induced in the metal surrounding the excitation coil produce fields at a considerable distance from the gradiometric sense coil, and are substantially attenuated compared to the signal due to the oscillating member.

Second, in the more interesting instance, the excitation coils are wound coaxially with the sense coils, in that each excitation coil also has two sections, in which both sections are wound in the same direction.

Furthermore, the first section of the sense coil is wound over the first section of the excitation coil, and the second section of the sense coil is wound over the second section of the excitation coil.

When this whole assembly is embedded in a metal or other electrically conductive matrix, each section of the excitation coil induces eddy currents in the surrounding material, with these eddy currents being of substantially the same spatial distribution for each section. Likewise, these eddy currents induce magnetic fields which are also of the same spatial distribution for each section. However, since the corresponding sense coils are wound in opposite directions and are placed in series, the voltage induced in each section by the eddy current fields are in opposition, and the net effect is that the signals due to the eddy currents are cancelled out by the gradiometric coil. This description also applies when the two aforementioned excitation coils are wound in axial proximity to one another, thus effectively constituting a single excitation coil.

Even in the absence of proximate conductive material, this coil configuration has the advantage of largely suppressing the voltages that would otherwise be induced in the sense coil by the excitation signal. This is particularly advantageous when using sense coils with a very large number of windings, as the coil assembly operates as a transformer with a large turns ratio. The excitation coil functions as a primary winding in this transformer, and induces a large voltage in the sense coil which constitutes the secondary winding. Since it is desirable in many applications to use high amplification factors in the successive stages of the amplifier chain in the sensing circuit, blocking the large voltages induced by the excitation coil can cause unwanted spurious signals that can interfere with the sensed signals due to the resonator's vibration.

A desirable enhancement to the sense circuit is to introduce passive amplification in the form of a step-up impedance matching transformer. Audio transformers with turns ratios in excess of 15:1 are readily commercially available. However, when such transformers are subjected to the large transients due to the excitation signal, they also produce secondary transients that tend to persist into the sensing period. It is therefore desirable to use the gradiometric sense coil arrangement to supply the sense signal to the matching transformer, in order to substantially reduce the applied sense voltage during the excitation phase, and the consequent persistent transients that would otherwise interfere with the sense signal.

These measures are particularly important as the overall electromagnetic sensitivity of the system is increased, with such increase being of particular interest when it is desirable to operate resonant measuring instruments over a large range of mechanical amplitudes, as may be the case in using, say, a resonant viscometer to measure fluid characteristics over several decades of shear rates.

Operating Principle of Gradiometric Coil

Referring to the system 10 of FIG. 1, a first magnetic dipole 12 having strength m1 and a second magnetic dipole 14 having strength m2 are shown at two different distances r1 and r2 (16 and 18) from a magnetic pickup coil 20. The dipoles 12 and 14 are shown with double arrows to indicate that their fields are sinusoidally oscillating, as in the case of a small permanent magnet that is vibrating either rotationally or translationally. A sinusoidal signal will be induced in the pickup coil 20 depending on the magnitude of the oscillating component of the dipole field. In other words, the system is insensitive to the static (DC) field produced by the dipoles 12 and 14.

Equation 1 gives the field B due to a magnetic dipole of magnitude m, measured along a line or length r perpendicular to the dipole axis, where k is a proportionality constant. The field B is inversely proportional to the third power of the distance between the dipole and the coil.

$$B = k*m*\frac{1}{r^3}. \qquad \text{Equation 1}$$

This strong dependence on r is advantageous, but at times insufficient to shield a transducer sense coil from outer magnetic influences, particularly when very high levels of transducer sensitivity are desired. For instance, for a single coil, if r1=10 mm and r2=100 mm, the ratio of signals due to two dipoles both of strength m will be 1000:1.

Figure 2:
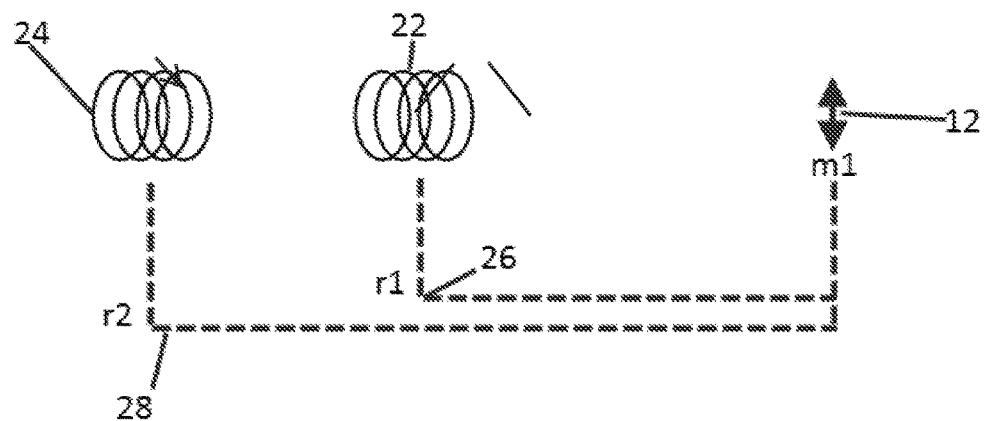
FIG. 2 is an illustration of distances from a single magnet to two different coils, to further explain the concept of a gradiometric coil.

An added measure of rejection of unwanted fields can be achieved by using two coils 22 and 24, spaced axially a short distance from one another, and wound in opposite directions, and connected in series, so that the signal produced by one coil, at distance r1 26 from dipole of strength m1 12, is subtracted from the signal produced by the second coil, at distance r2 28 from dipole of strength m1 12, as shown in FIG. 2.

The net signal is given by Equation 2, or the difference in flux at the positions of the two coils.

$$B = k*m*\left(\frac{1}{r_1^3} - \frac{1}{r_2^3}\right). \qquad \text{Equation 2}$$

This difference is the near-field behavior for dipole sources close to the gradiometric coils 22 and 24, or for distances between coils 22 and 24 to source and between coils 22 and 24 which are of the same order of magnitude. Consider the same conditions as above—a system in which there are two sources, one of which is 10 mm and the other 100 mm from the coil system—but now in which there are two coils in opposing series connection, so that their combined output is proportional to the difference in B fields at the locations of the two coils. If the first coil 22 is 10 mm from the source, and the second 24 is 5 mm from the first coil 22 (a reasonable situation for sensors considered in this application), then the coil pair still delivers 0.7 times the signal that would be delivered by the single coil 20. However, at a distance of 100 mm, the coil pair delivers only 0.13 times the signal that the single coil 20 would deliver. Taking into account the attenuation of the near-field signal—the signal of interest of about 30%—there is still a large advantage to the gradiometric coil for attenuating interfering signals only 100 mm from the system.

Figure 3:
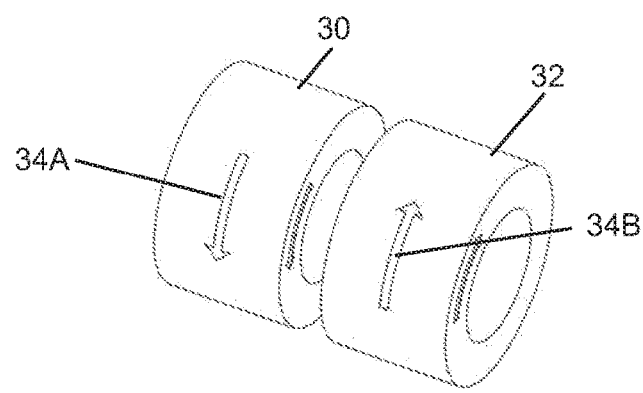
FIG. 3 is an illustration of a gradiometric coil.

FIG. 3 is a conceptual drawing of two coils 30 and 32 wound in opposite directions, indicated by the arrows 34A and 34B, which constitute a gradiometric coil when connected in series.

Figure 4:
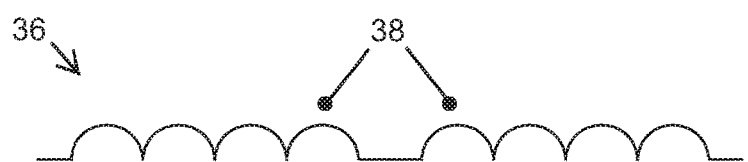
FIG. 4 is a schematic representation of a gradiometric coil.

As an electrical schematic, the gradiometric coil can be designated by a symbol 36 consisting of dots 38 at the end of each coil section to indicate the start of the winding, and connected winding starts to indicate the coils are wound to produce opposite signal polarities for the same varying magnetic field polarity, as shown in FIG. 4.

Gradiometric Coil as a Component in a Resonant Sensor System

Figure 5:
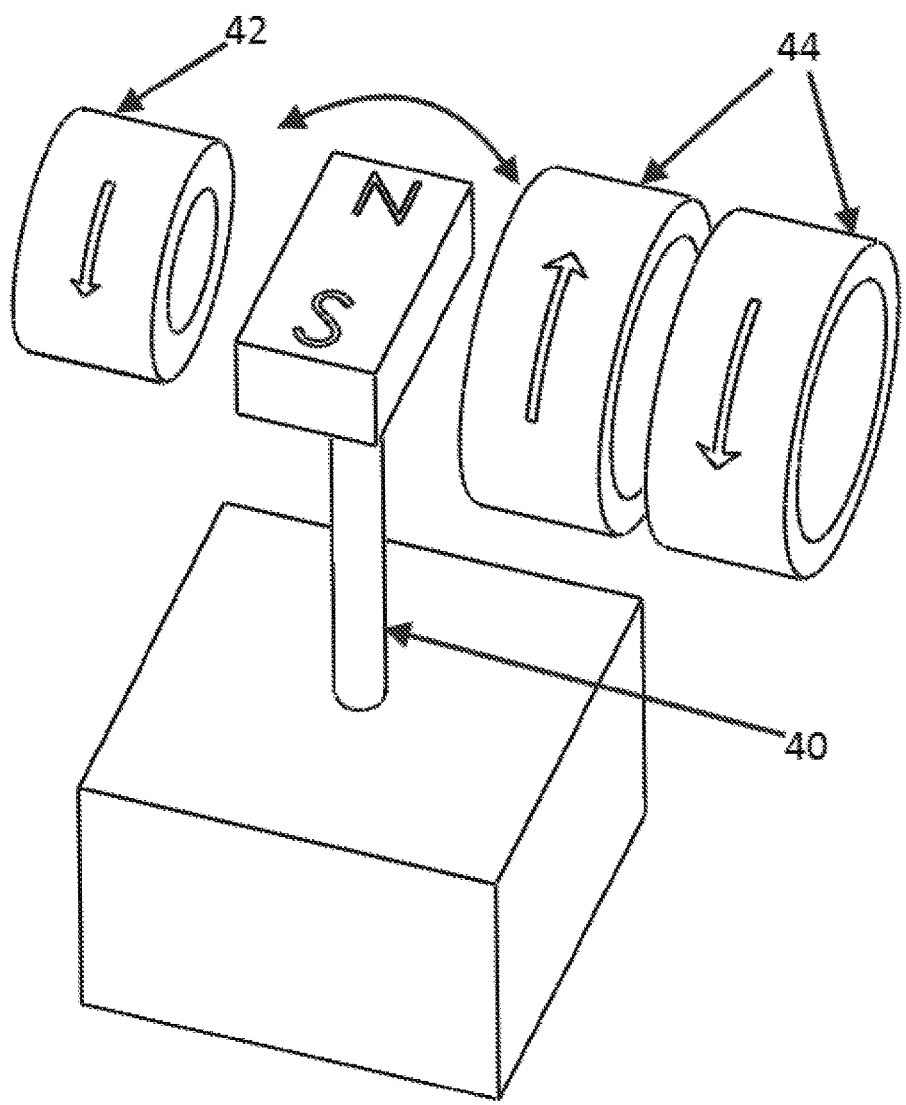
FIG. 5 is a top-front isometric view of a resonant fluid properties measurement assembly, according to a preferred embodiment of the present invention.

Referring to FIG. 5, an arrangement consisting of a lumped constant torsional resonator 40 and an arrangement of coils for exciting 42 and sensing 44 the vibrations of the resonator constitutes one of many possible embodiments of a resonant fluid properties measurement sensor.

Figure 6:
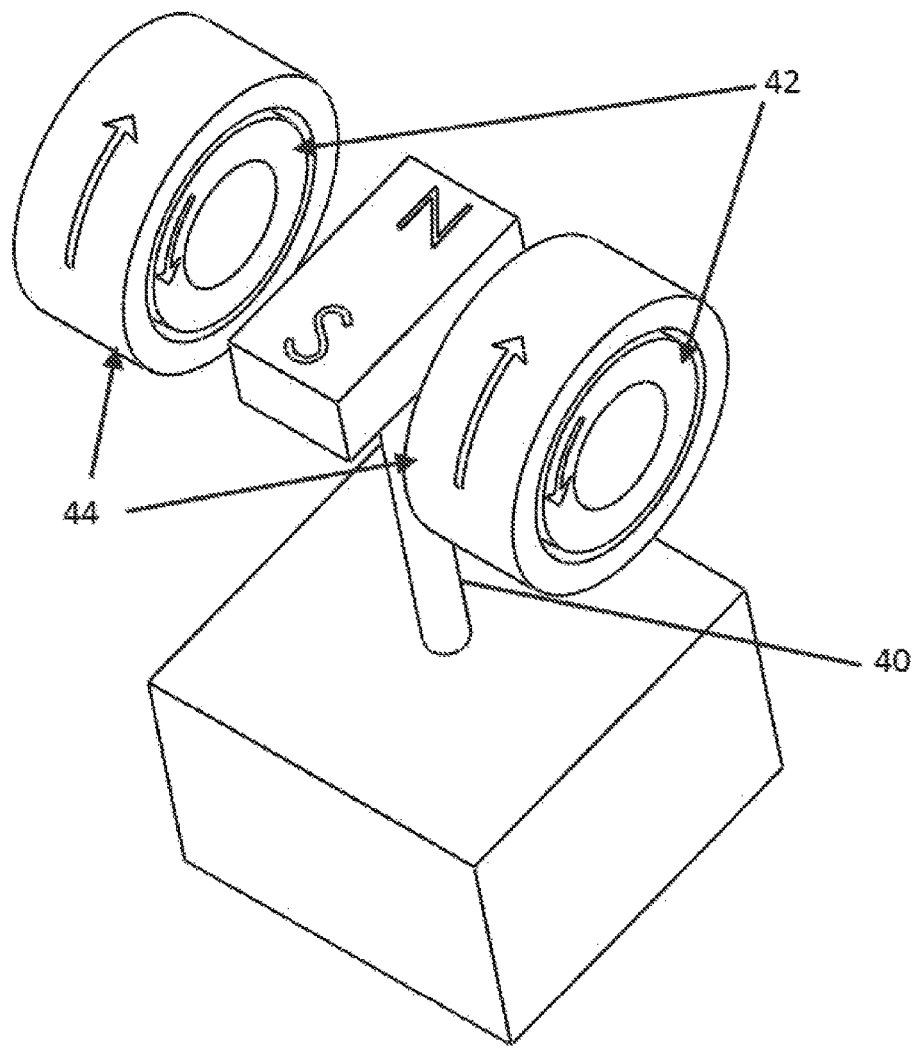
FIG. 6 is a top-front isometric view of a prior art resonant fluid properties measurement assembly.

This arrangement particularly lends itself to use of an electronics circuit for measuring the resonant frequency and damping of the resonator of the "gated phase locked loop" type, as disclosed, for instance, in U.S. Pat. No. 8,291,750. In that arrangement, the excitation coil 42 is periodically energized by a harmonic function, and the sense coil 44 is interrogated during pauses in the excitation. Because sensing and excitation are carried out in alternate time slots, there is in the ideal case no "crosstalk" between the excitation and sensing signals. This has permitted, for instance, installing both sense and excitation coils on both sides of the resonant element 40, leading to a four-fold increase in sensing efficiency, as well as other benefits from symmetrical excitation and sensing. A typical arrangement of this sort is depicted in FIG. 6 (Prior art).

This arrangement works well provided that the signal induced directly in the sense coils 44 by the excitation dies out completely before the sensed signal is measured. This condition can be violated under the following conditions:

1) The sense preamplifier stages are so overloaded that they do not recover completely before the sense signal must be measured. In that case, an excitation transient persists into the sensing period, causing distortion and effective crosstalk between the excitation and sensing.

2) It can be advantageous to use a transformer to match the usually low impedance of the sense coil 44 to the high input impedance of a low-noise differential preamplifier. Commercially available transformers are available that can provide up to about 15× voltage increase while adding only passive noise to the system. But the large currents induced in the sense coils 44 by the excitation signal can saturate the transformer's core, resulting in large transients that persist into the sensing period, again resulting in unwanted crosstalk.

3) In FIGS. 5 and 6, the coils 42 and 44 and resonator 40 are shown operating in free air, but in actual application, as in measuring fluid properties downhole in oil and gas exploration, drilling, and production, the whole system may need to be encased in metal. In that case, the excitation signal induces eddy currents in the metal matrix surrounding the coils 42 and 44. These eddy currents take time to die out, and persist well into the sensing phase, overwhelming the relevant sensor signal due to vibration of the resonator 40.

In actual practice, all three of these conditions may occur simultaneously. The arrangement of coils shown in FIG. 7 has been shown to be beneficial for eliminating excitation-to-sensing crosstalk, while maintaining high excitation and sensing efficiency under a variety of conditions. On each side of the resonator 40, both excitation coils 42 are wound in the same direction. Therefore, each contributes to the excitation field, although those closer to the resonator 40 are more effective than those further away. Each component coil of the gradiometric sense coil 44 surrounds its own section of the excitation coil 42. This means that the signals induced by the excitation in the sense coils 44 very nearly cancel out, although cancellation may not be perfect due to geometric imperfections in the coils 42 and 44 and their mounting. This nevertheless greatly reduces the overload of the sense preamplifier by the excitation signal. Furthermore, in the case that a matching transformer is used between the sense coils and the electronic preamplifier, this reduced feed-through of the excitation signal reduces the tendency to saturate the transformer core, thereby reducing persistent transients during the sense period.

Figure 7:
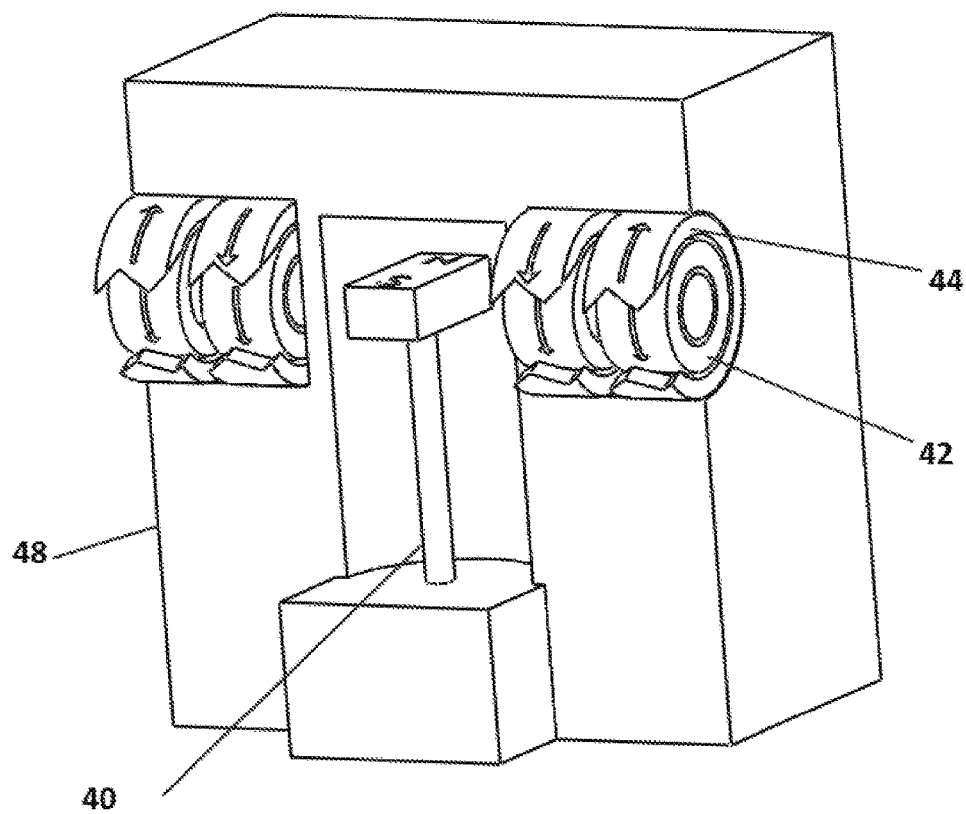
FIG. 7 is a top-front isometric view of a resonant fluid properties measurement assembly, according to an additional alternative preferred embodiment of the present invention.

In FIG. 7, the coils 42 and 44 are shown embedded in a metal casing 48 which is cut away to show internal relationships. In addition, the sense coils 44 are cut away to show the excitation coils 42 and the direction of their windings. Eddy currents are induced in the neighboring metal 48 by the excitation coils 42. In the above configuration, each excitation coil 42 produces approximately the same eddy current distribution in the metal surround. These eddy currents in turn induce equal and opposite voltages in the two sections of each gradiometric sense coil 44, thereby largely cancelling out the eddy current effects due to the excitation.

This configuration therefore improves the performance of the resonant system with its excitation and sensing coil system on all of the counts listed above that contribute to both preamplifier overload and cross talk effects between excitation transients and sensed signals from the resonator.

Figure 8:
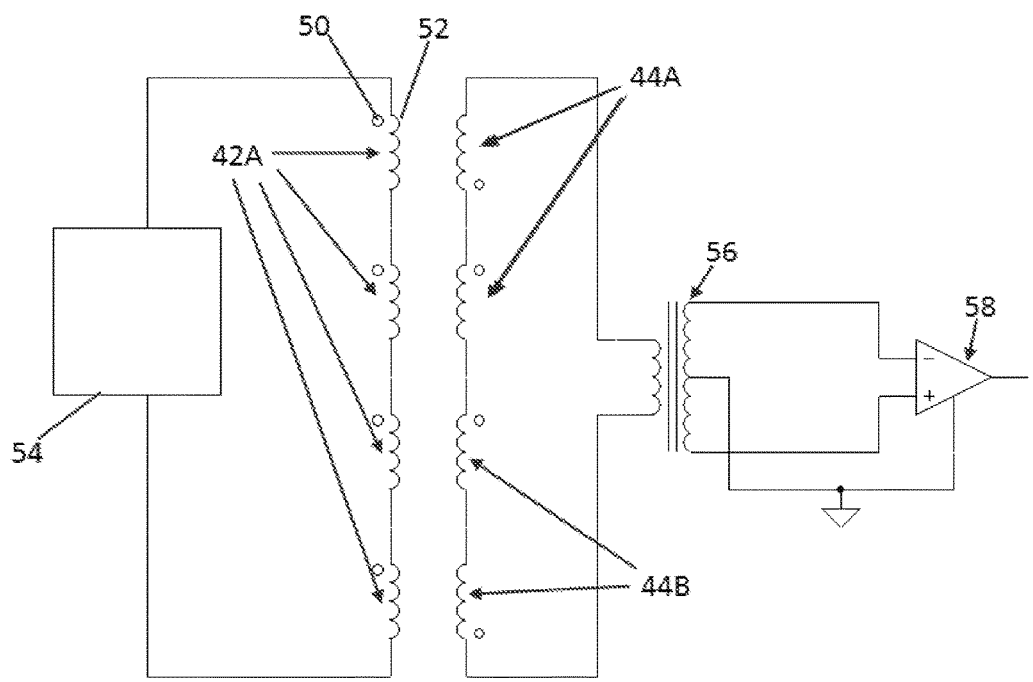
FIG. 8 is a schematic representation on one electrical network implementation of the fluid properties measurement assembly of FIG. 7.

FIG. 8 shows one of many possible circuit arrangements for optimizing the performance of the above-disclosed coil arrangements. The small circles 50 on the coil symbols 52 indicate relative polarity of the different coil sections, consisting of two gradiometric sense coils 44A and 44B and excitation coils 42A. The excitation circuit 54 is adjacent to the excitation coils 42A. The grounded center tap of the transformer 56 provides a return path for bias currents of the input stages of the differential signal amplifier 58.

Applicability to Other Resonator Configurations

All of the exemplary embodiments disclosed in this application are based on torsional resonators. All of these resonators were shown as operated by excitation coils supplying a field perpendicular to the magnetization of a permanent magnet attached to the resonator. The coils produce a torque on these magnets by producing a more or less uniform field that attempts to re-align the field of the resonator magnet in its direction.

Other configurations are possible, and for which the coil configurations shown in this application are equally valuable. These include:

1) transverse resonators, including tuning forks operating in the usual bending modes, leaf spring or other cantilever beams bending perpendicular to their own plane, or even magnetizable magnetic wires vibrating transversely, where excitation would function by means of attraction of a permanent magnet, or a ferri- or ferromagnetic material by the non-uniform field of an attracting coil, and sensing of such vibrations is typically done with a similar coil, with voltage in this coil being induced either by a permanent magnet attached to the resonator, or by a magnetic moment being induced in a ferri- or ferromagnetic resonator by an external polarizing coil; and 2) torsional resonators, in which torsion is produced and sensed by means of non-uniform fields acting directly on ferri- or ferromagnetic elements of the resonator as in (1) above, but acting tangentially to such elements so as to produce torsion instead of transverse motion.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A fluid properties measurement device, comprising:
   (a) a magnetically excited and sensed resonator;
   (b) a resonator electromagnetic excitation assembly, including a first and second excitation coil, said first excitation coil driven by an electrical network, electrically connected to said first excitation coil, said first excitation coil positioned so that a varying magnetic field produced by said first excitation coil will drive said resonator in a pattern of resonating movement that has predetermined characteristics;
   (c) an electromagnetic sensing assembly, including a first and second gradiometric sense coil, wherein said first gradiometric sense coil is coaxial with said first excitation coil, said second gradiometric sense coil is coaxial with said second excitation coil, and said first gradiometric sense coil is further positioned so that a magnetic field originating due to movement of said resonator in a pattern having said predetermined characteristics will create a time varying gradient across said first gradiometric sense coil; and
   (d) a signal sensing electrical network electrically connected to said first sense coil.

2. The fluid properties measurement device of claim 1, wherein said first excitation coil driving electrical network overlaps with and shares components with said signal sensing electrical network.

3. The fluid properties measurement device of claim 1, wherein said resonator is a torsional resonator.

4. The fluid properties measurement device of claim 1, wherein said first excitation coil is positioned on a first side of said resonator and said second excitation coil is positioned on a second side of said resonator and said first gradiometric sense coil is positioned on said first side of said resonator and said second gradiometric sense coil is positioned on said second side of said resonator.

5. The fluid properties measurement device of claim 1, wherein said first excitation coil and said first sense coil are positioned on a first side of said resonator and said second excitation coil and said second sense coil are positioned on a second side of said resonator opposed to said first side of said resonator.

6. The fluid properties measurement device of claim 5, wherein a first end, having a first polarity, of said first sense coil is electrically connected to a second end of said second sense coil, which has an opposite polarity to said first polarity of said first sense coil.

7. The fluid properties measurement device of claim 6, wherein said second end of said first sense coil is connected to said first end of said second sense coil through a transformer that drives a differential signal amplifier.

8. The fluid properties measurement device of claim 1, wherein at least one of the said first excitation coil, said second excitation coil, said first sense coil, or said second sense coil is embedded in a metal casing.

9. The fluid measurement device of claim 1 wherein each coil of the first sense coil surrounds a corresponding section of the first excitation coil, such that signals induced by the excitation in the sense coils are dampened.

10. A fluid properties measurement device, comprising:
(a) a magnetically excited and sensed resonator;
(b) a resonator electromagnetic excitation assembly, including an excitation coil driven by an electrical network, electrically connected to said excitation coil, said excitation coil positioned so that a varying magnetic field produced by said excitation coil will drive said resonator in a pattern of resonating movement that has predetermined characteristics; and
(c) an electromagnetic sensing assembly, including a first and second gradiometric sense coil each having a first end having a polarity, said first end of the first sense coil being electrically connected and having an opposite polarity to the said first end of said second sense coil, said first sense coil positioned so that a magnetic field originating due to movement of said resonator in a pattern having said predetermined characteristics will create a time varying gradient across said first sense coil; and
(d) a signal sensing electrical network electrically connected to said sense coil.

11. The fluid properties measurement device of claim 10, wherein said electrical network driving the excitation coil overlaps with and shares components with said signal sensing electrical network.

12. The fluid properties measurement device of claim 10, wherein said resonator is a torsional resonator.

13. The fluid properties measurement device of claim 10, wherein said excitation coil is a first excitation coil and is positioned on a first side of said resonator and a second excitation coil is positioned on a second side of said resonator.

14. The fluid properties measurement device of claim 13, wherein said first sense coil is positioned on said first side of said resonator and said second sense coil is positioned on said second side of said resonator.

15. The fluid properties measurement device of claim 13, wherein the first sense coil is coaxial with the said first excitation coil and said second sense coil is coaxial with said second excitation coil.

16. The fluid properties measurement device of claim 13, wherein said second side of said resonator is opposed to said first side of said resonator.

17. The fluid properties measurement device of claim 13, wherein said first excitation coil is coaxial with said second excitation coil and said first sense coil is coaxial with said second sense coil.

18. The fluid properties measurement device of claim 13, wherein a second end of said first sense coil is connected to a second end of said second sense coil through a transformer.

19. The fluid properties measurement device of claim 18, wherein said transformer drives a differential signal amplifier.

20. A device, comprising:
(a) a magnetically excited and sensed resonator having a first and an opposing second side;
(b) a resonator electromagnetic excitation assembly, including a first excitation coil driven by an electrical network, electrically connected to said first excitation coil, said first excitation coil positioned on said first side of said resonator so that a varying magnetic field produced by said excitation coil will drive said resonator in a pattern of resonating movement that has predetermined characteristics;
(c) an electromagnetic sensing assembly, including a a first gradiometric sense coil positioned on said first side of said resonator so that a magnetic field originating due to movement of said resonator in a pattern having said predetermined characteristics will create a time varying gradient across said sense coil;
(d) a second excitation coil and a second sense coil, also being a gradiometric coil, are coaxial and positioned on said second side of said resonator; and
(e) a signal sensing electrical network electrically connected to said first sense coil.

* * * * *